United States Patent
Rånby

[19]

[11] Patent Number: 6,156,530
[45] Date of Patent: Dec. 5, 2000

[54] METHOD FOR ANALYSIS OF HAEMOSTATIC ACTIVITY

[75] Inventor: Mats Gustaf Rånby, Umeå, Sweden

[73] Assignee: Global Hemostasis Institute MGR AB, Linköping, Sweden

[21] Appl. No.: 08/817,830

[22] PCT Filed: Nov. 8, 1995

[86] PCT No.: PCT/SE95/01324

§ 371 Date: Aug. 11, 1997

§ 102(e) Date: Aug. 11, 1997

[87] PCT Pub. No.: WO96/14581

PCT Pub. Date: May 17, 1996

[30] Foreign Application Priority Data

Nov. 8, 1994 [SE] Sweden ................................ 94303833

[51] Int. Cl.[7] ................ A61K 9/44; C12Q 1/56
[52] U.S. Cl. ............................ 435/40.5; 435/13
[58] Field of Search ................. 435/13, 4, 7.21, 435/326, 371, 372, 372.1, 372.2, 372.3, 383, 396, 174, 176, 177, 178, 179, 180, 181, 182, 40.5; 436/63, 68

[56] References Cited

U.S. PATENT DOCUMENTS

| | | | |
|---|---|---|---|
| 4,097,238 | 6/1978 | Ashley ........................ | 436/57 |
| 4,695,956 | 9/1987 | Leveen et al. ............... | 435/13 |
| 4,979,959 | 12/1990 | Guire ........................ | 623/66 |
| 5,051,239 | 9/1991 | Von Der Goltz .............. | 422/73 |

FOREIGN PATENT DOCUMENTS

| | | | |
|---|---|---|---|
| 0347933 A2 | 12/1989 | European Pat. Off. . | |
| 464135B | 3/1991 | Sweden . | |
| 93 00989 | 1/1993 | WIPO . | |

OTHER PUBLICATIONS

Francis et al. "Effec of the lupus anticoagulant on endothelial fibrinolytic activity in vitro," Thromb. Haemostasis (1989) 61(2): 314–317.

Greisler et al. "The effects of shear stress on endothelial cell retention and function on expanded polytetrafluoroethylene," Arch. Surg. (Dec. 1990) 125: 1622–25.

Kaibara et al. Rheological measurement of blood coagulation in vascular vessel model tube consisting of endothelial cells monolayer, Biorheology (1991) 28: 263–74.

Marieb, E. "Human Anatomy and Physiology," second edition, 1992, (Benjamin/Cummings Publishing: Redwood City, CA), p. 592–597.

Teitel et al., *Thrombosis and Haemostasis*, vol. 60, No. 2, 1988, 226–229.

*Primary Examiner*—Sandra E. Saucier
*Attorney, Agent, or Firm*—Bacon & Thomas

[57] ABSTRACT

This invention relates to a method of analyzing coagulative, fibrinolytic or haemostatic activity in, especially, blood or plasma from mammals, particularly humans. The method comprises bringing a sample, in vitro, into contact with fixed and preferably from their growth support detached endothelial cells or outer membranes of such cells, and detecting the resulting coagulated material and, in some cases, lyzed coagulated material. Reagents are also described that are based on the endothelial cells and their outer membranes. A kit for performing such a method including the claimed reagent is also described.

13 Claims, No Drawings

METHOD FOR ANALYSIS OF HAEMOSTATIC ACTIVITY

FIELD OF INVENTION

The present invention pertains, in general, to the field of haemostasis or to the study of the haemostatic system of mammals, in particular humans. More specifically, it pertains to a new, simple and thereby clinically useful analytical method which allows evaluation of either coagulative or fibrinolytic activity or even total haemostatic activity in a biological fluid. Primarily, this means analysis, in a simple yet reproducible and reliable manner, of blood or blood plasma in order to detect haemophilia and/or thrombophilia. The technique according to the invention is based on contact between the biological fluid and a reagent which effects the coagulative process, after which coagulated material is detected according to prior art principles. The novelty in relation to the invention is the utilization of a reagent that highly resembles the factors that in vivo effect coagulation in a mammalian individual, which gives better possibilities than the prior art to obtain a total picture of the haemostatic activity.

The invention also pertains to a kit for performing this method.

BACKGROUND OF THE INVENTION

Circulatory disturbances can lead to illness with bleedings or thrombi, clinical conditions which are denoted haemophilia or thrombophilia, respectively. Such disturbances may result from perturbations in the ability of the blood to coagulate or to dissolve coagulated material or from perturbations of the balance between these. Coagulum formation and coagulum dissolution are both precisely regulated processes, both of which can be regarded as composed of a driving and a restraining part. The coagulum-forming process is called coagulation and is hence a balance between pro-coagulative and anti-coagulative activities. Analogously, the coagulum dissolving process is called fibrinolysis and displays a pro-fibrinolytic and an anti-fibrinolytic part. The balance between coagulation and fibrinolysis is denoted haemostasis, which thus comprises all processes that prevent leakage of blood from the circulatory tract and which keep these open. The two concepts circulatory disturbances and haemostatic disturbances are in this context practically synonymous.

The understanding of haemophilia and the development of effective treatments for this condition has been strongly dependent on simple global functional laboratory methods, which have revealed altered coagulative properties of blood and blood plasma from the individuals in question. The principle of these methods is to add, to blood or blood plasma, reagents that trigger coagulation, and to register the reaction time necessary for a certain coagulum formation. Abnormally slow or weak coagulum formation has been characteristic of haemophilia, and medical treatments which have normalized the analytically determined values have proved to be effective in the alleviation of the clinical symptoms of the disease.

According to the above described view on hemostasis, the outlined prior art global functional laboratory methods for the characterizaton of coagulative activity are primarily sensitive to pro-coagulative disturbances. The methods have, however, appeared to be fairly satisfactory for the diagnosis of haemophilia because the haemostatic disturbances involved are often localized precisely to the pro-coagulative part of haemostasis. However, the prior art global methods cannot reveal disturbances in all haemophiliacs, and they are practically of no use for thrombophilia. This may be due to the fact that the methods do not give any indication, or only slight indication, of disturbances in the anti-coagulative part of the coagulation process, and that they lack sensitivity to fibrinolytic disturbances. The lack of or the need of a more comprehensive method, useful in practice, for analyzing or detecting coagulative, fibrinolytic and haemostatic properties of blood and blood plasma, is therefore obvious. A simple and especially a more reliable method relating to global haemostasis would doubtless result in improved diagnostics, improved treatment and more efficient development of methods of treatment, especially of thrombophilia. The present invention provides an improved global laboratory method of diagnostic analysis of coagulative, fibrinolytic or haemostatic properties of blood and blood plasma. Moreover, the method is of such nature that it is directly applicable to corresponding analysis of other biological fluids wherein such activities are present, for example synovial fluid and brain liquor.

DESCRIPTION OF THE INVENTION

The present invention thus provides a method of analysis of biological fluid from a mammalian individual, in particular human, for the purpose of determining or analyzing coagulative activity or fibrinolytic activity in a mammalian individual or even the total or global haemostatic activity in said fluid. In other words, it is possible, according to the invention, to identify individuals having disposition for haemophilia as well as individuals having disposition for thrombophilia by using one and the same method of analysis. Moreover, this can be achieved according to the invention in a most simple manner by performing the analysis in in vitro on very small amouts of sample of the biological fluid in question. This makes the method according to the invention particularly well suited for laboratory diagnostic use.

The method according to the invention is based on the surprising discovery that devitalized endothelial cells or devitalized and from their support liberated endothelial cells trigger coagulation in a biological fluid, especially in blood and blood plasma, in such a manner that haemostatic disturbances typical for both haemophilia and thrombophilia can be detected. Moreover, it has been discovered that the coagulated material, which is formed when the biological fluid is contacted with devitalized endothelial cells, can serve as a substrate for the fibrinolytic activity of the biological fluid which therefore can be analyzed and characterized according to the invention. This in turn makes it possible, as will be detailed below, to analyze and characterize a quantity that can be identified with haemostatic activity. Thus, it has been discovered that devitalized endothelial cells, and devitalized and from there their support liberated endothelial cells, posses considerable diagnostic potential with regard to haemostatic disturbances.

Nothing has hitherto been revealed about the properties of endothelial cells and their interactions with biological fluids, particularly blood and blood plasma, (see Stern et al. 1985, Proc. Natl. Acad. Sci. 82, 2523–2527 and Kirchhofer et al. J. Clin. Invest. 93, 2073–2082) that would initiate the use of these cells in in vitro laboratory diagnostic context. The generally accepted view that endothelial cells are strongly anti-coagulative should refrain a man skilled in the art from attempting to use endothelial cells in such diagnostic contexts where coagulative or fibrinolytic or haemostatic properties of a sample are to be analyzed. At least it can be established that the diagnostic potential of endothelial cells in this context has neither been concieved nor observed. As example of prior art, EP-A-538 951 can be mentioned. Therein, the difference between tissue factor and thromboplastin activity between cells from extra-cellular tissue and endothelial cells is mentioned, i.e. endothelial cells have been considered useless in the context contemplated by the present invention.

Nevertheless, according to the present invention it is shown that endothelial cells can be fixed and detached from their support, or vice versa, and that these fixed endothelial cells still posses activities of such nature that they are useful as a main component in reagents for analysis or characterization of coagulation, fibrinolysis and haemostasis in a mammalian individual. The nature of the reagent used in the method of the invention will thereby be very close to the reality in that coagulation under the influence of a system of co-operating and opposing factors are studied according to the invention in stead of some factor or a few factors disconnected from their context. The fact that detachment of the endothelial cells from the support on which they have been cultured or allowed to grow apparently does not harm the, in this context, active membrane structure, allowes the present invention to utilize the effects mentioned, in a particularly advantageous way, in already existing equipment. For example, the new reagent according to the invention can be used in regular coagulation instruments as a particulate suspension or can be used to coat a solid surface to immobilize the particulate preparation. Still, the method according to the invention comprises also the case when the endothelial cells used are not detached from their original place of growth, even though this, in many cases, means that full advantage of the surprising discovery of the activity in question of the fixed and detached cells, is not obtained.

The method according to the invention is thus a method of analysis, particularly quantitative analysis, of coagulative, fibrolytic or haemostatic activity in a biological fluid, especially blood or blood plasma, from a mammalian individual, in particular human, wherein the characteristic feature of the method is contacting a quantity of sample of said fluid, in vitro, with fixed and preferably from their place of growth detached endothelial cells, or outer membranes of such cells, and detecting the resulting coagulated material, preferably by measuring the time required for a certain amount of coagulum to form or by measuring the amount of coagulum formed during a certain period of time. Both before and after the coagulum-lytic activities of the sample have had the opportunity to be expressed, detection of the resulting coagulated material can be done and, this proves to be more advantageous, the result of the lytic processes is detected.

More specifically an aspect of the invention is directed to a method of analysis, particularly quantitative analysis, of coagulative, fibrinolytic or haemostatic activity in to a biological fluid, especially blood and blood plasma, from a mammalian individual, especially human, wherin a quantity of a sample of biological fluid, especially blood or blood plasma, is brought into contact in vitro with fixed and preferably from their place of growth detached endothelial cells, or outer membranes of such cells, and either a) the rate of coagulum formation or the time required for a certain amount of coagulum to form is determined, this rate or coagulation time being compared with reference values of rates and coagulation times of normal individuals, and if this rate or coagulation time is shorter than the reference values the sample of biological fluid is likely to come from an individual having disposition for thrombosis, whereas if the rate or coagulation time is longer than the reference values then the sample of biological fluid is likely to come from an individual having disposition for bleeding, or b) the coagulative processes are disrupted and the amount of coagulum formed during a certain contact time is determined, the amount of coagulum being compared with reference values of amounts of coagulum of normal individuals, and if the amount of coagulum is smaller than the reference values then the sample of biological fluid is likely to come from an individual having disposition for bleeding, whereas if the amount of coagulum is greater than the reference values then the sample is likely to come from an individual having disposition for thrombosis, or c) the coagulative processes are disrupted after a certain time and an additional certain reaction time is allowed, followed by determination of the amount of dissolved coagulated material, this amount of dissolved coagulated material being compared with reference values of dissolved coagulated material of normal individuals, and if the dissolved amount of coagulated material is greater than the reference values then the sample of biological fluid is likely to come from an individual having disposition for bleeding, whereas if the dissolved amount of coagulated material is smaller than the reference values then the biological fluid is likely to come from an individual having disposition for thrombosis, or d) the coagulative processes are disrupted after a certain time and an additional certain reaction time is allowed, followed by determination of the residual amount of coagulated material, this amount of residual coagulum is compared with reference values of amounts of residual coagulum of normal individuals, and if the amount of residual coagulum is smaller than the reference values then the sample of biological fluid is likely to come from an individual having disposition for bleeding, whereas if the amount of residual coagulum is greater than the reference values then the biological fluid is likely to come from an individual having disposition for thrombosis.

When the procedural step a) or b) is performed, results pertaining to coagulative activity are obtained. When the procedural step c) is performed, results pertaining to fibrinolytic activity are obtained, and when the procedural step d) is performed results pertaining to haemostatic activity are obtained. Alternatively, the fibrinolytic, or coagulum-lytic, activity can be identified as the difference between assay results obtained in b) and d).

In one embodiment of the invention, the amount of sample of the biological fluid is previously reversibly anti-coagulated blood or blood plasma, which in connection with the mentioned in in vitro contact is returned to its coagulation-active state. Thus, for exemple, the fluid, which can be blood or blood plasma, is anti-coagulated with a substance that binds $Ca^{2+}$ ions, preferably citrate or EDTA, and the return to its coagulation-active state is accomplished by addition of excess amounts of $Ca^{2+}$ ions. Alternatively, the fluid may be anti-coagulated with a coagulation-inhibiting substance, e.g. hirudin or heparin, and the return to the coagulation-active state is accomplished by addition of a substance which inhibits the effect of said coagulation-inhibiting substance, for exemple antibodies that inhibit the activity of hirudin or heparinase, respectively.

Conveniently, the analysis is performed on an amount of sample of biological fluid of maximally 1.0 mL, preferably 0.01–1.0 mL. Most preferably the amount of sample is maximally 0.2 mL, and the coagulation time is maximally 15 minutes.

In performing the procedural step b), c) or d), the coagulative processes may be disrupted by the addition of a coagulation-inhibiting substance, which preferably is chosen from the group consisting of hirudin and heparin but also $Ca^{2+}$ ion complexing agents such as citrate, oxalate or EDTA are possible.

In performing the procedural step a) or b), the analysis may be performed in the presence of a fibrinolysis-inhibiting substance, which preferably is chosen from the group of 6amino-hexanoic acid and antibodies against tPA and uPA.

The result of performing the procedural step a), can be obtained by detecting coagulated material by means of measuring changes in the optical or rheological properties of the reaction mixture, preferably changes in light transmission or viscosity.

The results of performing the procedural step b), c) or d) can be obtained by detecting coagulated material by measuring some component or degradation product of the coagulated material preferably fibrin or thrombocytes. Conveniently, results in this regard are obtained by measuring the amount of fibrin via its enzymatic degradation, preferably by plasmin, to soluble degradation products, which are measured with immunological technique. So, for exemple, said degradation products may be measured with an immunological technique which is specific for D-dimer fragments, or the amount of thrombocytes associated with fibrin may be measure by flow cytometry after enzymatic degradation of the fibrin.

Another aspect of the invention is directed to a reagent for the analysis of coagulative, fibrinolytic or haemostatic activity of a biological fluid, especially blood or blood plasma, from a mammalian individual, especially human, which reagent is composed of suspended or support-attached endothelial cells or outer membranes from such cells.

In an embodiment of of this aspect of the invention, the endothelial cells or their outer membranes are from an individual of the same species as the individual whose biological fluid is to be analyzed, preferably from the same individual and most preferably from the part of the body which is subjected to said analysis.

In another embodiment, the endothelial cells or their outer membranes are immobilized on a solid phase. In order to stabilize the active surface structures, polyethylene ethers or polysaccharides can be covalently bound to the outer membranes of the endothelial cells.

Yet another aspect of the invention is directed to a kit for performing a method of analysis of coagulative, fibrinolytic or hemostatic activity in a biological fluid, especially blood or blood plasma, from a mammalian individual, especially human, which kit comprises, as a coagulation reagent, a reagent according to the invention and instructions for performing the method.

According to the invention, it has been shown that devitalized (other commonly used denotation; fixed) or devitalized and detached from their support (other commonly used denotation; suspended) endothelial cells can be used to characterize coagulative, fibrinolyfic and hemostatic activity of biological fluids, especially blood and blood plasma, and that this can be accomplished in a diagnostically valuable manner, i.e. so that individuals with circulatory diseases can be differentiated from normal individuals. Functions typical for the living endothelial cell, such as excretion, endocytosis and modifications of outer membrane structures, re obviously not necessary in order for endothelial cells to trigger activities in biological fluids that make meaningful diagnosis possible. From this it is obvious th also isolated outer membranes from endothelial cells can be used in practising the invention. Thus, the use of such outer membranes does not represent any deviation from the spirit of the invention, and in this context even synthetically manufactured structures characteristic for the surface of endothelial cells may be contemplated. In other words, the expression "outer membranes of such cells" should interpreted broadly and it encompasses all attempts to (also synthetically) arrive at membrane-like structure that triggers the same or similar activities in biological fluids, especially blood and blood plasma, as fixed or fixed and suspended endothelial cells.

The fixed endothelial cells used in the method according to the invention, can be obtained from different sources and can be prepared in different ways without deviating from the original idea of the invention. Endothelial cells can, for example, be obtained from cultured cells which in accordance with known methodology have been detached from the interior surface of umbilical cord veins. Placenta is another possible source of endothelial cells as are established cell lines of transformed endothelial cells. It should be understood that an effective preparation according to the invention, of fixed or fixed and from their support detached endothelial cells, does not necessarily need to be totally homogeneous. It is sufficient that a main constituent of a cell preparation according to the invention is endothelial cells.

Preferably such endothelial cells are chosen that are from an individual of the same species as the individual from whom the biological fluid is obtained. More preferably the endothelial cells are from the same individual and most preferably from the part of the body which is subject to analysis according to the invention. Choosing endothelial cells from the same individual as from whom the sample of biological fluid is obtained would allow detection also of circulatory disturbances that stem from abnormalities of this individual's endothelial cell structures that together with this individual's biological fluid express disturbances in coagulative, fibrinolytic and/or hemostatic activity.

In the preparation of endothelial cells from cultures of such cells, it is possible to detach these cells from the support on which they grow, so that a mainly monodisperse suspension is obtained. The cells can, for instance, be detached by citrate or an other substance that binds $Ca^{2+}$ ions and can thereafter be fixed. Other methods for detaching the endothelial cells, e.g. by use of EDTA, are also within the scope of the invention. If the cells are detached from their support with the aid of enzymes, it may be necessary to culture the cells for some time before they are fixed, in order to allow necessary surface structures to reform. Different methods for fixation of cells are certainly previously known in the prior art.

These methods are applicable also in the present case, but preferably in the method according to the invention the endothelial cells are devitalised or fixed with substances chosen from the group of formalin and STF™ fixation solution.

The invention is nether restricted to the case where the cells are at first fixed and thereafter detached from their support. The reverse course of action is fully possible within the scope of the invention.

Specific analysis of coagulative, fibrinolyfic or haemostatic activity is possible according to the invention but may require additions of coagulation-inhibiting or fibrinolysis-inhibiting substance, which will be described in detail below.

As preferred examples of coagulation-inhibiting substances hirudin and heparin can be mentioned, and as preferred examples of fibrinolysis-inhibiting substances 6-amino-hexanoic acid and antibodies against tPA and uPA can be mentioned.

A considerable advantage with regard to the use of fixed endothelial cells according to the invention, is that these can be utilized in the form of a suspension, preferably a water-based suspension, which enables the use of equipment for detection of coagulation existing on the market. As examples of such equipment, coagulation instruments operating with liquids or suspensions and wherein detection of coagulum formation most often is performed photometrically, may be mentioned.

The in vitro contact between the fixed endothelial cells, or outer membranes, and the biological solution is, however, not restricted to the use of suspensions but can be accomplished by using other principles known per se. For example, the contact can be accomplished with endothelial cells or outer membranes immobilized on a solid phase preferably of the micro test plate type.

Immobilization on the solid phase can preferably be accomplished via binding of biotin to the endothelial cells or outer membranes, and thereafter coupling to the surface of the solid phase by means of biotin-binding substances, preferably streptavidin.

According to yet another preferred embodiment of the method according to the invention, preparations of endothelial cells, preferably suspended, or corresponding outer membranes, with increased stability and homogeneity are obtained in case the endothelial cells are treated with reactive compounds that covalently bind hydrophilic substances to the outer membrane structures of the cells. As preferred examples of such stability- and homogeneity-improving compounds polyethylene ethers and polysaccharides may be mentioned. Thus, such improved stability and homogeneity are extremely valuable in a method of the present kind, wherein the analysis is dependent on reasonably stable reagents.

Coagulated material that results from performing the method according to invention, is preferably detected by means of measuring changes in the optical or Theological properties of the reaction mixture, especially in case the use of cells in suspension is involved. Preferably, this concerns changes in light transmission and viscosity, respectively.

Coagulated material can according to another embodiment be detected by means of measuring changes in the interactions of the reaction mixture with magnetic, electric or electromagnetic fields. This methodology is particularly suitable for working with cells immobilised on a solid phase.

Coagulated material is preferably detected via the components it contains or is made up of, particularly fibrin and thrombocytes.

The amount of fibrin can preferably be measured by enzymatic degradation of the same, preferably by plasmin, to soluble degradation products which are measured with immunological technique. A preferred such technique is a technique specific for D-dimer fragments.

Another preferred embodiment of the invention measures the amount of thrombocytes associated to the thrombocytes, for example by flow cytometry. This can be accomplished after the coagulum has been enzymatically degraded, i.e. has been lyzed.

As indicated above, the method according to the invention is primarily intended for analysis of blood and blood plasma but is in no way restricted to this and can be applied in any instance where activities of the corresponding type exist.

For the analysis to be useful in practice in clinical contexts, this implies that, in the method, the use is made of previously reversibly anti-coagulated blood or blood plasma which is returned to the coagulation-active state in dose connection with the contacting in vitro which, according to the invention, is performed with fixed endothelial cells or corresponding active components of these.

One preferred embodiment involves blood or blood plasma that has been anti-coagulated with substances that bind $Ca^{2+}$ ions, preferably citrate or EDTA, and that the return to the coagulation-active state is accomplished by addition of $Ca^{2+}$ ions in excess.

Another interesting embodiment requires that the blood or blood plasma is anti-coagulated with a coagulation-inhibiting substances of hirudin or heparin type and that the return to the coagulation-active state is accomplished by addition of agents that inhibit the effects of the anti-coagulative substances in question, preferably antibodies, that neutralize the activity of hirudin, and heparinase, respectively, that degrades heparin into inactive saccharides.

For a method of clinical laboratory utility it is moreover required that it must be operable on small quantities of sample. This requirement is fulfilled in the present case, since the method according to the invention can be performed on such small amounts of sample. According to one preferred embodiment of the invention this means that the analytical method is performed on an amount of sample that is smaller than 1.0 mL, preferably 0.01–1.0 mL.

For laboratory diagnostic utility, especially on larger scale, it is furthermore required that the analytical method should not be excessively extended in time. Coagulative activity may according to the invention be determined in less than 15 minutes and fibrinolytic and haemostatic activity within 90 minutes.

The invention also pertains to a kit for performing an analytical method of the type defined above, the characterizing feature of said kit being that it contains a coagulation reagent comprising the above mentioned endothelial cells or outer membranes of these, and instructions disclosing how the method is to be performed.

DETAILED DESCRIPTION OF THE INVENTION

The invention will be further illustrated below by means of a number of concrete practical examples, which however do not in any way restrict the scope of the invention. Before these are presented in detail, a short background of the methods and materials used will be given as follows.

Methods which today are commonly used for laboratory detection of coagulative properties of blood and blood plasma are denoted activated prothrombin time, APTT, prothrombin time, PT, and prothrombin complex time, PTK. These methods are based on the use of one or two reagents, which are mixed with the sample of blood or blood plasma, which is thereby coagulated. The speed with which the reaction mixture coagulates constitutes the assay response. Often time in question is measured from the moment of reagent addition up to a certain coagulum formation. This is detected by measuring a certain change in the optical properties of the reaction mixture or a certain change in its rheological properties.

The analyses are often performed on samples that are anti-coagulated by addition of citrate or other substances that bind $Ca^{2+}$ ions, which are necessary for the coagulation processes. The reagents contain $Ca^{2+}$ ions which restore the coagulative ability of the samples. If non-anti-coagulated samples are to be analyzed, the reagents need not contain $Ca^{2+}$ ions as sufficient amounts of these are present in the blood sample.

The APTT reagent contains silica particles, and the PT- and PTK-reagents contain tissue factor preparations. Both of these reagents contain phospholipids.

With the above described generally used methods, blood and blood plasma from individuals without circulatory disturbances display normal coagulation times while samples from haemophiliacs display prolonged coagulation times. Samples from thrombophiliacs, almost without exception, display normal coagulation times.

According to one aspect of the method according to the invention, Individuals without circulatory disturbances display normal coagulation times, while individuals with haemophilia often display abnormally long coagulation times and individuals with thrombophilia in many cases display abnormally short coagulation times.

In one embodiment of the procedure according to the invention, a reagent composed of fixed endothelial cells suspended in aqueous solution containing $Ca^{2+}$ ions is used. When this reagent is mixed with blood or blood plasma anti-coagulated with citrate, longer than normal coagulation times are obtained for most haemophiliacs and shorter than normal for many thrombophiliacs. The coagulation times are a measure of the coagulation activity of the blood plasmas. With an identical method coagulation activity can in a similarly advantageous manner be determined for blood and other biological fluid such as synovial fluid and liquor.

Coagulative activity of anti-coagulated blood, blood plasma or other biological fluid can be analyzed and characterized also with other embodiments of the method according to the invention. According to one such embodiment, an anti-coagulated sample of the biological fluid is added to small containers, e.g. wells of micro test plates, the surface of which carry fixed endothelial cells. Once the sample has been returned to a coagulative state by the addition of substances that neutralize the anti-coagulative effect, the coagulative processes are allowed to proceed for a certain time after which they are halted by addition of coagulation-inhibiting substances such as hirudin or heparin. The amount of coagulated material is thereafter measured. Either the amount of fibrin or the number of thrombocytes in the coagulated material is measured. The amount of fibrin can be measured by enzymatically degrading this to soluble degradation products, followed by measurement of the amount of these by immunological techniques. The number of thrombocytes in the coagulated material can be determined, e.g. with flow cytometry, after the thrombocytes have been liberated from the coagulated material by enzymatic degradation of the same. It should be mentioned that, if the fibrinolytic activity of the sample is considerable, disturbances of the analysis of coagulative activity can be avoided by addition of fibrinolysis-inhibiting substances to the sample prior to analysis. The fixed endothelial cells on the inner surface of the reaction vessel can either be cultured on this site or, which is more practical and better exploits the possibility of the invention, be immobilized thereon from preparations of fixed and from their support detached endothelial cells.

The invention also allows for analysis of the fibrinolytic activity of the sample solution. For this purpose the coagulated material is first allowed to form under a certain time. Thereafter, the reaction is stopped by addition of coagulation-inhibiting substances, e.g. EDTA, hirudin or heparin, after which sufficient time is allowed for the results of the fibrinolytic activity of the sample to become measurable as increase of the amount of fibrin degradation products. It is pointed out that the fibrinolytic activity in a sample of biological fluid often is unstable. This can be caused by inhibitory activities, particularly plasminogen activator inhibitor type I (PAI-1), and can require special sample collection and sample handling techniques. Thus, for exemple, the pH of the sample can be immediately reduced to between 5.8 and 6.0 (see Ranby et al 1989, Thromb Haemostas 62, 917–922) to prevent reaction between tPA and PAI-1. For analysis according to the invention of such acidified samples, sufficient amounts of pH-raising substances may be added in order to avoid hampering of the coagulative and fibrinolytic processes. Correct assessment of the fibrinolytic activity may also require addition of substances that prevent said reaction after the pH has been neutralized. An example of such a substance is inhibitory antibodies towards PAI-1.

An analytical method that resembles the latter application of the invention enables an assay response that can be identified with haemostatic activity. Hereby the coagulative activity is first allowed to express for a certain time during which an amount of coagulated material in proportion to the coagulative activity is formed, whereupon the coagulative processes are stopped by the addition of a coagulation-inhibiting substance. Thereafter, the fibrinolytic activity is allowed to act under a sufficient time for creation of a measurable reduction of the amount of coagulated material. The amount of coagulated material that then remains constitutes a measure of the balance between coagulation and fibrinolysis, i.e. the hemostatic activity. The amount of coagulated material is measured as the amount of fibrin and/or as the number of coagulum-associated thrombocytes, as previously described.

The method according to one embodiment of the present invention is based on the use of reagents that are mixed with samples in principally the same manner as in the analysis according to the methods of APTT, PT and PTK. The coagulation times are registered in the same manner as in these methods.

EXAMPLES

Materials

Human endothelial cells from umbilical cord were prepared from 30 to 40 cm long umbilical cords from full term foetus. The umbilical cords were obtained from the maternity ward, the University Hospital of Linköping, Sweden. Prior to preparation, the umbilical cords were stored for not more than 24 hours at 2–4° C. in sterile PBS (phosphate buffered saline) with penicillin and gentamycin. During preparation the umbilical cord vein was, rinsed with about 50 mL of sterile PBS containing penicillin and gentamycin, filled with cell culture medium A (Dulbeccos Minimal Essential Medium, 1% non-essential amino-acids, 2% 200 mM L-glutamine, 1.2% 100 mM/20 IU/mL oxalo-acetic acid/insulin, 12% foetal calf serum and 0.1% penicillin-streptomycin) containing 500 mg/L collagenase, closed at both ends with Péans and incubated for 15 minutes at 37° C., whereupon it was massaged for 2 minutes. The contents of umbilical vein including 25 mL of rinse (medium A) were transferred to a 50 mL test tube, which was centrifuged for 5 minutes at about 500 xg for sedimentation of the endothelial cells. The supernatant was discarded and the endothelial cells suspended in 10 mL of medium A. The endothelial cells were again allowed to sediment by centrifugation for 5 minutes at 500 xg, after which the supernatant was discarded and the cells were suspended in 5 mL of medium A and transferred to a 23 cm² cell culture flask with gelatin treated bottom surface. This primary culture was incubated for 2 to 4 days at 37° C. in an atmosphere containing 5% $CO_2$. When the cells had developed into a confluent monolayer, verified microscopically, they were passaged. The passage indicates that the cell culture medium was discarded and the cells detached from their support by treatment with minimal amount of 10 g/L trypsin dissolved in 0.15 M NaCl and 5 mM EDTA. The detached endothelial cells were suspended in 10 mL of medium A and seeded into two cell culture flasks each with a gelatin-treated bottom surface of about 23 cm². At confluence, after 2 to 4 days of culture, the cells were passaged a second time and seeded out in four cell culture flasks with gelatin-treated bottom surface of 23 cm² each. For some experiments, the endothelial cells were seeded out in about 50 micro test plate wells with gelatine treated bottom surfaces. When these cells, in the following called HUVEC (human umbilical vein endothelial cells), within 2 to 4 days formed a confluent mono-layer, they were used in the examples below.

Gelatin treatment of cell culture flasks and micro test plate wells was performed in such manner that the bottom surfaces were covered with 0.2% gelatin in water, incubated for 15 minutes, emptied of excess and allowed to air dry.

For Example 1 were used: suspended devitalized (fixed) endothelial cells, that were obtained by washing the HUVEC cells in one cell culture flask with PBS and detaching them from their supporting place of growth by 15 minute incubation at 37° C. in 4 mL of 0.1 M ($Na^+$) citrate buffer pH 7.3 with an addition of 0.05 mL of 20 mM TM-PEG.

For Examples 4 and 5 were used: suspended fixed endothelial cells, to which biotin was conjugated. These were obtained by incubating HUVEC in one 23 cm² cell culture flask for 30 minutes at 37° C. with 2 mL of 21 mM Hepes buffer pH 8.2 with 105 mM sodium citrate and 2 mM $CaCl_2$ with an addition of 0.05 mL of TM-PEG and 0.05 mL of 2 mg/mL of NHS-biotin. The cells were detached with a small cell rubber policeman. The so suspended cells were fixed for 30 minutes at room temperature by the addition of 4 mL of STF fixation solution (se below) and washed by three fold repeated centrifugation and re-suspension in 0.02 M Hepes buffer pH 7.5 with 0.1 M NaCl. Suspended, fixed, biotin conjugated HUVEC were immobilized on the surface of streptavidin-treated micro test plate wells (Labsystems product 95029290) by the addition to each well of about 4,000 cells suspended in 0.1 mL of 0.02 M Hepes buffer with 0.1 M NaCl and incubated for 18 hours at room temperature.

For Examples 2 and 3, HUVEC cultured in micro test plate wells were used. They were washed two times in PBS and devitalized by addition of 0.1 mL of 0.1% formalin in PBS per well and incubated for 10 minutes at room temperature with subsequent twice repeated wash with 0.2 mL PBS.

Samples of blood plasma were obtained from the Laboratory of Clinical Chemistry, University Hospital of Linköping with generous support of Dr. Tomas Lindahl. Samples with known APTT- and PTK-values were obtained within 4 hours of routine analysis with the reagents and instruments used by the laboratory during June 1994. The same laboratory also generously supplied citrate anti-coagulated samples from individuals without known haemostatic disorders, i.e. from healthy (normal) individuals. These samples from patients and normal individuals were stored at −70° C. for a maximum of 5 months prior to use.

Reagents for the determination of D-dimer (a degradation product of fibrin) with ELISA technique, 1241 TintElize D-dimer, and latex technique, 150707 Minutex D-dimer, were obtained from Biopool AB, Umeå, Sweden.

tPA, tissue plasminogen activator with single-chain structure, single-chain tPA, product 122101 from Biopool AB, was dissolved in 0.5 M ($Na^+$) Hepes-buffer pH 8.5 to a concentration of 3,000 IU/mL.

Hirudin, product 53000, was obtained from American Diagnostics Inc., Greenwich, Conn. Hirudin was dissolved in $H_2O$ to a concentration of 100 ATu/mL.

Heparin, 100 IU/mL for injectional use, was obtained from Løvens kemiske fabrik, Ballerup, Denmark.

STF (Streck Tissue Fixative) containing diazolidinyl-urea, 2-bromo-2-nitro-propane-1,3-diol, zinc sulphate and citrate, was obtained as ready to use solution from Streck Laboratories Inc., Omaha, Nebr., USA.

TM-PEG (metoxypolyethylene-glycol-tresylate), product M-3038, was obtained from Sigma Chemical Company, St. Louis, Mo., USA.

NHS-LC-biotin (sulphosuccinimidyl-6-(biotiamido) hexanoate), product 21335, was obtained from Pierce, Rockford, Ill., USA.

NaCl, $CaCl_2$, Hepes, citric acid, formalin and 6-amino-hexanoic acid were of high commercial quality. Water of high purity was obtained from an apparatus employing ion-exchange and reversed osmosis serviced by the Department of Clinical Chemistry, University Hospital Linköping.

Example 1

The invention was practised for analysis of coagulative activity with a protocol resembling a one-step prothrombin analysis according to Quick, wherein 1 volume of citrate anti-coagulated plasma was mixed with one volume of thromboplastin reagent containing $CaCl_2$ and registration of coagulation time was performed.

This experiment utilized a commercial Quick reagent, 50220 Thromboplastin from Biopool AB, Umeå, composed of a suspended extract from delipidated rabbit brain tissue. A corresponding reagent according to the invention was HUVEC reagent 1, which contained $0.2 \times 10^6$ cells/mL of suspended fixed HUVEC in 50 mM Hepes buffer pH 7.3 containing 15 mM $CaCl_2$, 30 g/L PEG 6000, 30 g/L BSA and 2 g/L Triton X-100. The analyses were performed with a coagulation instrument with photometric detection of coagulum formation, Coagulator 4, Behnk Elektronik, with 0.15 mL of sample and 0.15 mL of reagent, both temperature equilibrated at 37° C.

The following citrate anti-coagulated samples were analyzed:

Pooled plasma from normal individuals (NP) and NP diluted 1:2 (NP50%) and NP 1:4 (NP25%) with a barbiturate buffer with citrate and NaCl (Tampon pour SPA, Diagnostica Stago, Franconville, France). Moreover the following were analyzed: a plasma sample with a PTK-value below 25% (PTK<25%) and a plasma sample (TRBP) from a thrombotic patient. The plasma sample PTK<25% was pooled from individuals treated with vitamin-K antagonists who according to analysis performed during April–May 1994 by the Laboratory for Clinical Chemistry, University Hospital Linköping, showed PTK-values of less than 25%. The results of the analysis with Quick-reagent and HUVEC-reagent 1 are depicted in the table below, where the results have been placed in order of precedence according to their coagulation times and with the coagulation time in seconds given within parenthesis.

| Quick-reagent | | HUVEC-reagent 1 | |
|---|---|---|---|
| NP | (12.9) | TRBP | (214.1) |
| TRBP | (13.4) | NP | (233.7) |
| NP50% | (17.1) | NP50% | (282.6) |
| PTK<25% | (23.1) | NP25% | (383.2) |
| NP25% | (25.6) | PTK<25% | (459.4) |

It may especially be noted that TRBP has a longer coagulation time than NP in analysis with the Quick-reagent, while TRBP has a shorter coagulation time than NP with analysis according to the invention, HUVEC-reagent 1.

A plasma sample from a thrombophiliac thus displays a shortened coagulation time in analysis according to the invention. This is not the case with conventional analysis. Diluted normal plasma as well as pooled plasma with long coagulation times according to other conventional method (PTK) display prolonged coagulation ) times both with analysis according to the invention and with conventional Quick-methodology. However, analysis according to the invention seems to more clearly distinguish PTK<25% than is the case with the Quick-reagent. To summarize, in the displayed experiment, analysis according to the. invention gives more relevant diagnostic information about thrombophilia than does conventional analysis, and at least as good information on haemophilia.

For purposes of confirmation, the same thrombotic plasma (TRBP) and the same pool of normal plasma (NP) were analyzed on a later occasion, and then with another HUVEC-reagent and another commercial preparation of thromboplastin reagent (IL Test PT-fibrinogen, product 97567-10, Instrumentation Laboratories, Milano, Italy). The analysis according to the invention was performed with HUVEC-reagent 2 and HUVEC-reagent 3, which differed only in that they contained $0.23 \times 10^6$ cells and $0.46 \times 10^6$ cells/mL, respectively. The experiment with HUVEC-reagent 3 was performed in duplicate in the same instrument channel. Other experimental details were identical to those detailed above. The following results were obtained with the coagulation times denoted in seconds.

|      | Quick-reagent | HUVEC-reagent 2 | HUVEC-reagent 3 |
| ---- | ------------- | --------------- | --------------- |
| NP   | 12.3          | 381.0           | 436.8 and 438.9 |
| TRBP | 12.6          | 277.5           | 208.4 and 236.6 |

Hereby confirmation was obtained, that coagulation analysis according to the invention can differentiate the plasma from a thrombotic patient from that of a normal individual in a case where conventional analysis is without diagnostic effect.

Example 2

Quantitative analysis of coagulative activity according to the invention is here applied on citrate anti-coagulated plasma from 10 patients referred to the Department of Clinical Chemistry, University Hospital Linköping, for investigation concerning cause of thrombotic disease and on the same type of samples from 10 healthy individuals, i.e. individuals who have never been afflicted with thrombotic disease.

In the analysis, a sample of size 0.10 mL was added to a micro test plate well, the bottom surface of which was covered with a confluent layer of fixed HUVEC. The reaction was started by addition of 0.010 mL of 0.5 M $CaCl_2$ and allowed to proceed minutes at room temperature under agitation on a shaking apparatus with circular eccentric movement, 1 mm eccentricity and 200 revolutions per minute. The reaction was stopped by addition of 0.010 mL of 20 ATu/mL of hirudin. The wells were emptied of their contents and washed three times with 0.25 mL of 0.15 M NaCI. Cell-associated fibrin was dissolved with 0.1 mL of human serum with 300 IU/mL of tPA which was allowed to act for 20 minutes at room temperature after which the amount of D-dimer in the serum was determined by ELISA. The following results, presented in order of precedence according to increasing content of D-dimer, were obtained:

| Thrombotic patients D-dimer (ng/mL) | Healthy individuals D-dimer (ng/mL) |
| ----------------------------------- | ----------------------------------- |
| 75                                  | 73                                  |
| 77                                  | 78                                  |
| 77                                  | 88                                  |
| 83                                  | 89                                  |
| 215                                 | 99                                  |
| 366                                 | 119                                 |
| 577                                 | 179                                 |
| 952                                 | 193                                 |
| 1849                                | 467                                 |
| 2553                                | 470                                 |

Four of the 10 thrombotic patients displayed higher, three considerably higher, amounts of fibrin associated with endothelial cells than any of the healthy individuals, when blood plasma from these were analyzed according to the invention. Statistical analysis also showed that the groups most probably differed from each other $p<0.05$ according to one-tailed t-test. Analysis according to the invention of coagulative activity according to this example displays some of the diagnostic possibilities of the procedure.

Example 3

Quantitative analysis of coagulative activity according to the invention with the same protocol as in Example 2 was performed on seven blood plasma samples anti-coagulated with citrate. These samples had been analyzed less than 2 hours earlier on May 18 1994 according to PTK and APTT by the Laboratory of Clinical Chemistry, University Hospital Linköping. The results for these seven samples are shown below in order of precedence according to their PTK-times. PTK-values in percent are given within parentheses. D-dimer according to the invention.

| PTK (s)    | APTT (s) | D-dimer (ng/mL) |
| ---------- | -------- | --------------- |
| 19.4 (145) | 35.3     | 368             |
| 24.1 (91)  | 45.3     | 296             |
| 25.0 (84)  | 31.7     | 334             |
| 29.7 (59)  | 39.7     | 198             |
| 31.0 (54)  | 47.3     | 195             |
| 44.9 (29)  | 33.4     | 149             |
| 59.1 (20)  | 48.5     | 130             |

Linear regression analysis shows that coagulation activity according to the invention shows that good negative correlation with PTK-times and similar good positive correlation with PTK-values in percent. A negative correlation with APTT-times is also evident This result indicates that coagulation analysis according to the invention can find use in diagnostic contexts where PTK- and APTT-analyses are used, i.e. in the identification of individuals with bleeding tendencies and in guiding and monitoring of substitution therapy for haemophiliacs and therapy for thrombosis prophylaxis with oral anti-coagulants (warfarin) or subcutaneous anti-thromboticum (heparin).

The correlation between analysis according to the invention and PTK and APTT are both better than that between PTK and APTT. This high-lights the over-all, global, character of the analysis according to the invention.

Example 4

Quantitative analysis of coagulative activity according to the invention, but with a protocol that differs in several details from that of Example 3, was applied to blood plasma anti-coagulated with citrate from four thrombotic patients and one healthy individual. According to this protocol, 0.10 mL of plasma was added to micro test plate wells coated with streptavidin with attached devitalized fixed biotin-conjugated endothelial cells or, as control, to similar wells but without cells. The coagulation reaction was initiated by addition of 0.025 mL of 0.15 M $CaCl_2$ and was stopped by 0.025 mL of 100 IU/mL heparin. The amount of fibrin formed was determined quantitatively by addition of 0.025 mL of 3000 IU/mL of tPA, which under 20 minutes was allowed to process formed fibrin into soluble degradation products. These were measured as D-dimer by ELISA.

The results of the analysis, D-dimer in ng/mL, are presented below, where the value for the well containing endothelial cells is denoted "with HUVEC" and the control well "without HUVEC". The difference is given as "with-wihout":

|  | with HUVEC | without HUVEC | with-without |
| --- | --- | --- | --- |
| Thrombotic patient 1 | 188 | 142 | 46 |
| Thrombotic patient 2 | 933 | 140 | 853 |
| Thrombotic patient 3 | 2836 | 174 | 2662 |
| Thrombotic patient 4 | 3597 | 52 | 3545 |
| Healthy individual | 2487 | 227 | 2260 |

In this example two of the four thrombotic patients (patient 3 and patient 4) displayed greater fibrin deposit on the endothelial cells that the healthy individual. Thrombotic patient 1 displayed markedly low D-dimer development although fibrin deposition was verified microscopically. Perhaps this is a thrombotic patient with reduced ability to degrade fibrin in spite of high levels of plasminogen activator.

Example 5

Quantitative analysis of fibrinolytic activity according to the invention was demonstrated with a series of five blood plasma samples from a healthy individual, to which small volumes of concentrated tPA solution was added so that the final addition of tPA activity was 0, 0.73, 2.9, 11.7, and 46.7 IU/mL Of these tPA enriched plasmas, 0.10 mL was added to micro test plate wells with attached endothelial cells of the same kind as was used in Example 4. A limited amount of fibrin was formed during 7 minutes upon addition of 0.025 mL of $CaCl_2$.

The fibrin formation was stopped by addition of 0.025 mL of 100 IU/mL of heparin, after which the fibrinolytic reactions were allowed to continue for an additional 60 minutes. The amount of fibrin degradation products thus formed was used as a measure of the fibrinolyfic activity and was determined as D-dimer in the well contents by ELISA. The results were the following:

| Sample | added tPA (IU/mL) | D-dimer (ng/mL) |
| --- | --- | --- |
| A | 0 | 41 |
| B | 0.73 | 42 |
| C | 2.9 | 45 |
| D | 11.7 | 317 |
| E | 47 | 3640 |

The example shows that analysis according to the invention can be used for analysis of fibrinolytic activity. Plasma with high levels of tPA display high levels of D-dimer.

What is claimed is:

1. A method of diagnosing thrombophilia in a mammal comprising: contacting, in vitro, a sample of blood or plasma of an individual suspected of having a thrombophilic disorder with fixed endothelial cells or outer membranes of fixed a) determining the rate of coagulum formation or the time required for the formation of a predetermined amount of coagulum, comparing the rate or time with a reference value from blood or blood plasma obtained from normal individuals, wherein if the rate is faster or the coagulation time is shorter, the sample is assessed to come from an individual having disposition for thrombosis or b) halting the coagulation, determining the amount of coagulum, and comparing the amount of coagulum with reference values of amounts of coagulum obtained from normal individuals, wherein if the amount of coagulum is greater than the reference values the sample is assessed to come from an individual having disposition for thrombosis, or c) halting the coagulation, allowing coagulum dissolving reactions to continue, determining the amount of dissolved coagulum, comparing the amount of dissolved coagulum with reference values of dissolved coagulum obtained from normal individuals, wherein if the dissolved amount of coagulum is smaller than the reference values the sample is assessed to come from an individual having disposition for thrombosis, or d) halting the coagulation, allowing coagulum dissolving reactions to continue, determining the amount of remaining coagulum, comparing the amount of remaining coagulum with reference values of remaining coagulum obtained from normal individuals, wherein if the amount of remaining coagulum is greater than the reference values the sample is assessed to come from an individual having disposition for thrombosis.

2. The method according to claim 1, wherein said sample of blood or blood plasma is prior to the contacting with fixed endothelial cells or outer membranes of fixed endothelial cells reversibly anticoagulated, and returned to a coagulable state at said contacting in vitro.

3. The method according to claim 2 wherein said sample of blood or blood plasma is anticoagulated with citrate or EDTA that binds $Ca^{2+}$ ions, and returned to coagulable state by addition of $Ca^{2+}$ ions.

4. The method according to claim 2, wherein said sample of said blood or blood plasma is anticoagulated with a coagulation-inhibiting substance selected from hirudin or heparin, and that said return to coagulable state is accomplished by addition of antibodies which neutralize the coagulation-inhibiting activity of said hirudin, or by addition of heparinase to neutralize the coagulation-inhibiting activity of said heparin.

5. The method according to claim 1, wherein the determination is performed on a quantity of blood or blood plasma of 0.01–1.0 ML.

6. The method according to claim 1, wherein, during the determination, the coagulation is halted by the addition of a coagulation-inhibiting substance, which is selected from the group consisting of hirudin and heparin.

7. The method according to claim 1, wherein the determination is performed with a fibrinolysis-inhibiting amount of a fibrinolysis-inhibiting substance added to the reaction mixture, which substance is selected from the group of 6-amino-hexanoic acid and antibodies against tPA and uPA.

8. The method according to claim 1, wherein the coagulum is detected by means of changes in optical or rheological properties of the reaction mixture, including changes in light transmission or viscosity.

9. The method according to claim 1, wherein the coagulum is detected by measuring some component or degradation product of the coagulum, selected from fibrin, thrombocytes, or soluble degradation products of fibrin.

10. The method according to claim 9, wherein the amount of thrombocytes in the coagulum is measured after enzymatic degradation of the coagulum.

11. The method according to claim 1, wherein the amount of fibrin is measured via its enzymatic degradation with plasmin, to soluble degradation products, which are measured with immunological technique.

12. The method according to claim 11, wherein said degradation products are measured with immunological technique specific for D-dimer fragments.

13. The method of claim 1 wherein said mammal is a human.

* * * * *